United States Patent [19]

Doyle et al.

[11] Patent Number: 5,302,737
[45] Date of Patent: Apr. 12, 1994

[54] SILYCARBONYLATION OF 1-ALKYNES

[75] Inventors: Michael P. Doyle; Michael S. Shanklin, both of San Antonio, Tex.

[73] Assignee: Trinity University, San Antonio, Tex.

[21] Appl. No.: 996,360

[22] Filed: Dec. 23, 1992

[51] Int. Cl.⁵ .............................. C07F 7/08
[52] U.S. Cl. .................................... 556/436
[58] Field of Search ........................ 556/436

[56] References Cited

U.S. PATENT DOCUMENTS 4,568,566  4/1986  Tolentino ........................ 427/54.1
5,124,468  6/1992  Krafft et al. .................... 556/436

FOREIGN PATENT DOCUMENTS 0229450  1/1989  European Pat. Off. .
0362860  4/1990  European Pat. Off. .
0363252  4/1990  European Pat. Off. .
0425121  5/1991  European Pat. Off. .

Primary Examiner—Paul F. Shaver
Attorney, Agent, or Firm—P. S. Kalyanaraman

[57] ABSTRACT

This invention provides a process to regioselectively silylcarbonylate 1-alkynes and in predominantly the Z-isomer with substantial absence of hydrosilylation by-products. The process involves reacting a 1-alkyne with an organosilane and carbon monoxide in a solvent in the presence of a catalyst. The catalyst is a carboxylate salt of a metal such as rhodium, iridium or rhenium.

21 Claims, No Drawings

SILYCARBONYLATION OF 1-ALKYNES

FIELD OF THE INVENTION

This invention relates to a novel process for regioselectively silylcarbonylating 1-alkynes using carbon monoxide, an organosilane and a suitable carboxylate catalyst such as, for example, dirhodium (II) perfluorobutyrate, $Rh_2[CF_3(CF_2)_2CO_2]_4$. The process of the present invention substantially avoids the formation of hydrosilylated by-products, and results in high yield of the desired silylcarbonylated product in the preferred isomeric form.

BACKGROUND OF THE INVENTION

Silylcarbonylation, also called silylformylation, of acetylenes (alkynes) has been studied extensively, due to its potential for forming reaction products that are useful in synthesizing novel organic molecules and pharmaceutical intermediates. For example, I. Matsuda et al, *J. Amer. Chem. Soc.*, Vol. 111, 2332 (1989) report the silylcarbonylation of alkynes with carbon monoxide and a silane using a catalyst such as $Rh_4(CO)_{12}$. When the silane is a trialkylsilane, the product generally formed by way of the Matsuda et al process is in both isomeric forms, the Z-and the E-forms, and with little regioselectivity of addition. In order to get regioselectivity of addition, phenyldimethylsilane is used.

I. Ojima et al, *Organometallics*, Vol. 10, 38 (1991) report a similar reaction catalyzed by Rh-Co mixed metal carbonyl clusters. Depending on the nature of the silane used, the product is reported to be either a silylcarbonylated product only or a mixture of silylcarbonylated and hydrosilylated products. Trialkylsilanes generally gave a mixture of both, while phenyldimethylsilane gave the silylcarbonylated product exclusively with regioselectivity of additiG6 on and in the Z-form.

Due to the commercial significance of silylcarbonylated products, there is a continuing interest in identifying improved methods to prepare such compounds from low cost starting materials which is an object of the present invention.

It is a further object of the present invention to have such reactions yield the silylcarbonylated product, without substantial contamination by hydrosilylated product.

It is another object of this invention to form a silylcarbonylated product from alkynes substantially as one isomer (the Z- or the E- isomer) and with regioselectivity of addition, by a catalytic process wherein the catalyst enables the applicability of a wide range of silanes.

SUMMARY OF THE INVENTION

It has now been found that regioselective silylcarbonylation of 1-alkynes may be achieved with substantial absence of hydrosilylation by-products, by reacting 1-alkynes with a suitable organosilane and carbon monoxide, using a suitable carboxylate salt of rhodium, iridium or rhenium as catalyst. The process advantageously results in stereoselectivity also whereby the Z-isomer of the silylcarbonylated product predominantly forms. The inventive process comprises mixing and reacting the 1-alkyne, the organosilane, the catalyst and carbon monoxide in a suitable solvent, and separating the silylcarbonylated product. In the context of the present invention, the term "predominantly forms" means that the ratio of the Z-isomer to the Enisomer in the silylcarbonylated product ranges from about 5:1 to about 99:1. "Substantial absence of hydrosilylation by-products" means that not more than 10% hydrosilylation products are formed. Generally, as high as 99% of silylcarbonylated products are formed by the inventive process.

The reaction may be conducted at ambient (one atmosphere) pressure of carbon monoxide or optionally at higher pressures such as, for example 2–20 atmospheres. The reaction temperature and duration may vary with the pressure employed, as will be readily apparent to those skilled in the art. Typically, when the reaction is performed at higher than one atmosphere pressure of carbon monoxide, all reactants may be taken together in any order in a pressure vessel and reacted. Generally, the reaction times tend to be shorter in higher pressure reactions than at ambient conditions (one atmosphere pressure) reactions.

When the reaction is performed at low pressures, e.g., one atmosphere pressure of carbon monoxide, it is preferred to add the 1-alkyne to the other reaction mixture components, rather than vice versa. Such a preferred mode of addition results in regioselective silylcarbonylation as well as in predominant yield of the Z-isomer and reduces the formation of hydrosilylation by-products. In such cases, the process sequentially comprises:

(a) providing a first mixture comprising the catalyst, the organosilane, carbon monoxide and a suitable solvent;
(b) adding the 1-alkyne to the first mixture, and stirring under one atmosphere pressure of carbon monoxide; and
(c) separating the silylcarbonylated product formed in the reaction.

DESCRIPTION OF THE INVENTION

The present invention provides, in one embodiment, a novel process to regioselectively silylcarbonylate 1-alkynes, by employing a suitable organosilane, carbon monoxide, and a suitable carboxylate salt of rhodium, iridium or rhenium as catalyst. The reaction is depicted below:

$$R-C\equiv CH \;+\; CO \;+\; SiHR_1R_2R_3 \;\xrightarrow[\text{Solvent}]{\text{Catalyst}}$$

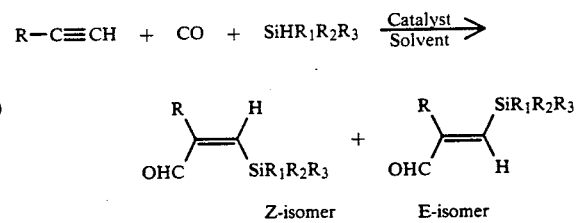

Z-isomer     E-isomer where $R_1$, $R_2$ and $R_3$ are moieties described below. The term 'regioselectivity' refers to the fact that while theoretically the two regioisomers $$R-C(CHO)=CH(SiR_1R_2R_3)$$

$$R-C(SiR_1R_2R_3)=CH(CHO)$$

may form in such silylcarbonylations, the inventive process selectively and predominantly produces the former silylcarbonylated derivative. The inventive process also results in high stereoselectivity. The term 'stereoselectivity' refers to the fact that in the inventive reaction, the ratio of the Z- isomer to the E-isomer is generally from about 5:1 to about 99:1.

The reaction is conducted in a suitable solvent. Suitable solvents are those that do not adversely react with the reagents employed and generally include solvents belonging to the classes of hydrocarbons, ethers, esters, halogenated hydrocarbons, amides, ketones and the like. Preferred solvents are of the ether, ester, halogenated hydrocarbons and amides type with halogenated hydrocarbons being the most preferred. Examples of suitable solvents include dichloromethane, dichloroethane, xylene, O-dichlorobenzene, N,N-dimethylformamide and the like.

As stated above, the silylcarbonylation may be conducted at one atmosphere pressure of carbon monoxide or optionally under higher pressures of carbon monoxide. The reaction conditions may be somewhat different in each case as will be appreciated by those skilled in the art. For example, higher pressure reactions will have to be conducted in a suitable pressure vessel. In any event, processes in accordance with the invention are catalyzed by carboxylate salts of rhodium, iridium or rhenium; examples include the acetate, butyrate, trifluoroacetate, perfluorobutyrate and like salts of such metals. Preferred are the salts of rhodium and the most preferred salt is rhodium (ii) perfluorobutyrate, $Rh_2[CF_3(CF_2)_2CO_2]_4$, hereinafter referred to as $Rh_2(pfb)_4$. Preparation of $Rh_2(pfb)_4$ has been reported by M. Doyle et al, *Inorg. Chem.*, Vol. 26, 3070 (1987). With respect to the instant invention, the catalyst is employed generally in amounts ranging from about 0.01 to about 1 mol % based on the amount of the 1-alkyne being reacted, preferably in about 0.1-1 mol %, and typically in about 0.1-0.5 mol %.

Organosilanes useful in connection with the present invention are of the formula $SiHR_1R_2R_3$, wherein $R_1$, $R_2$ and $R_3$ could be the same or different and are selected from the group consisting of hydrogen, a $C_1-C_6$ alkyl, a phenyl group, a naphthyl group and an alkoxy of the formula $-OR'$ wherein $R'$ is a $C_1-C_6$ alkyl, provided at least one of said $R_1$, $R_2$ and $R_3$ is not hydrogen. Examples of suitable organosilanes include triethylsilane, trimethylsilane, tributylsilane, triphenylsilane and phenyldimethylsilane.

The class of alkynes silylcarbonylated in the inventive process are 1-alkynes (terminal alkynes). Internal alkynes may also be silylcarbonylated by a similar procedure; however, 1-alkynes generally form the silylcarbonylated product predominantly in the Z-form with significant absence of hydrosilylation by-products in the inventive process, while internal alkynes generally yield hydrosilylation by-products. An alkyne useful in the invention is thus of the formula $R-C\equiv CH$, wherein R is a branched or unbranched $C_1-C_8$ alkyl, or a branched or unbranched $C_1-C_8$ alkoxy, or a substituted or unsubstituted phenyl or naphthyl moiety, wherein the substituents are selected from the group consisting of alkyl, phenyl, benzyl, benzoyl, alkoxy, acetamido, halo, hydroxy, dialkylamino, and acetoxy groups, wherein the alkyl component is a branched or unbranched $C_1-C_8$ alkyl moiety. Examples of suitable 1-alkynes are phenylacetylene, 4'-isobutylphenylacetylene, 6-methoxynaphthyl-2-acetylene, n-hexylacetylene, propargyl acetate, mechyl propargyl ether, 3-benzoylphenylacetylene, (3-fluoro -4phenyl)phenylacetylene, 3-hydroxy-3-methylbut-1-yne, 4'-tolylacetylene, 3-butyn-2-one and the like.

When the reaction is performed at low pressures, e.g., one atmosphere pressure of carbon monoxide, it is preferred to add the 1-alkyne to the other reaction mixture components, rather than vice versa as stated above. In an illustrative case, the silane and the catalyst are mixed in the solvent and kept stirring under carbon monoxide at a suitable temperature while the alkyne is added to the mixture. The reaction is generally performed at temperatures of about $-30°$ C. to about $200°$ C., preferably at about $-30°$ C. to about $100°$ C., and typically about $-10°$ C. to about $30°$ C. After the addition of the alkyne, the reaction mixture is stirred at the above-identified temperatures generally for about 1-100 hours, typically for about 5-80 hours, and preferably for about 24-72 hours. Isolation and analysis of the product may be achieved by techniques known to those skilled in the art. For example, the solvent may be removed by rotary evaporation to isolate the product. The product may be further purified by processes such as, for example, chromatographic techniques, if purification is desired. Analysis of the product and determination of the isomer ratio may be performed by gas chromatography, NMR spectroscopy, elemental analysis and the like.

When a higher pressure reaction is desired, the reactants may be mixed in any suitable order. Thus, for example, the alkyne, the silane, the solvent and the catalyst may all be taken together in a suitable pressure vessel such as, for example, an autoclave, and stirred under about 2-20 atmospheres pressure of carbon monoxide. Temperatures of about $-30°$ C. to about $300°$ C. may be employed for the reaction; generally higher temperatures tend to advantageously decrease the reaction time. Reaction times of about 0.5-100 hours may generally be employed. The yields of the desired product are generally comparable to those from the low pressure reaction described above. The product, after releasing the pressure from the vessel, may be isolated, purified and analyzed in the same manner as above or by other customary techniques.

A preferred embodiment of the present invention may be illustrated by the following description of the preparation of α-phenyl-β-triethylsilyl acrolein (Formulas IIA and IIB, indicating the Z and the E isomers respectively) from phenylacetylene (Formula I):

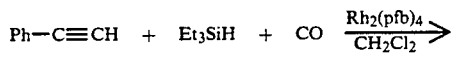

I

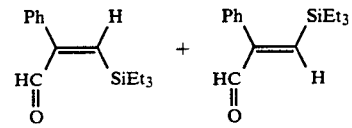

II A          II B

Thus, triethylsilane (available from Aldrich Chemical Co., Milwaukee, Wis.; about a molar equivalent to compound of formula I) and $Rh_2,(pfb)_4$ (about 0.3 mol % based on compound of Formula I) may be combined in a suitable solvent such as, for example, dichloromethane. Carbon monoxide is passed into the vessel and maintained at one atmosphere and the temperature of the reaction mixture is lowered to about $0°-5°$ C. Phenylacetylene (available from Aldrich Chemical Co.)

dissolved in a solvent such as, for example, dichloromethane, is added dropwise to the stirring reaction mixture. The reaction mixture may be stirred for about 24 hours, after which the solvent is removed by a suitable process such as distillation. The product may be purified, if necessary, by distillative techniques, and analyzed. In a typical experiment, product yields of more than 80% were achieved, wherein the silylcarbonylated derivatives IIA and IIB predominated demonstrating regioselective addition. Only traces (less than 1%) of hydrosilylated products could be detected. Furthermore, the Z:E ratio (IIA:IIB) was found be almost 10:1, thus demonstrating the stereoselectivity also.

The following Examples are provided in order to further illustrate the present invention; however, the invention is in no way limited thereby.

EXAMPLES

In the following Examples, g refers to grams, ml to milliliters, °C. to degrees Celsius, mol to moles, and mmol to millimoles.

Example I. Preparation of α-phenyl-β-triethylsilyl acrolein (Formulas IIA and IIB) using ambient pressures of CO: In a 100 ml flask fitted with a thermometer, a syringe pump for addition and a gas inlet and outlet and containing $Rh_2(pfb)_4$ (0.3 mol % based on phenylacetylene) in dichloromethane (50 ml) under atmospheric pressure of carbon monoxide was added triethylsilane (0.29 g, 2.5 mmol), and the reaction mixture was kept stirring under an atmosphere pressure of carbon monoxide (ambient pressure) while being cooled to about 0°-5° C. At that temperature, a solution of phenylacetylene (0.26 g, 2.5 mmol) in dichloromethane (5 ml) was added via the syringe pump over about 4-5 hours. After this time the product separated from the catalyst by column chromatography and the solvent was distilled off. Less than 1% of hydrosilylation product was detected. Purification was performed by vacuum distillation. Yield: 82%, with a 10:1 Z:E ratio.

Example II. Preparation of α-(4'-isobutylphenyl)-β-phenyldimethylsilyl acrolein: This compound was prepared from 4'-isobutylphenylacetylene, phenyldimethylsilane, and $Rh_2(pfb)_4$ in dichloromethane under an atmosphere pressure of carbon monoxide by following a process similar to that described in Example 1. The desired silylcarbonylated product was formed in 74% yield with a Z/E isomer ratio of 11:1. Again, as in Example 1, the hydrosilylation product formed in negligible (<1%) yields.

In a similar manner, various other alkynes and silanes were used in the reaction. Results are shown in Table 1, as Examples III through VIII.

When internal alkynes were employed in place of terminal alkynes, generally more hydrosilylation products were formed. Examples IX and x in Table 1 illustrate this.

Example XI. Preparation of αphenyl-β-triethylsilyl acrolein (Formulas IIA and IIB) using a higher than ambient pressures of CO: In a PYREX reaction vessel (300 ml capacity) in a stainless steel autoclave, phenylacetylene (1.02 g, 10 mmol), triethylsilane (1.16 g, 10 mmol), $Rh_2(pfb)_4$ (0.3 mol% based on phenylacetylene) and dichloromethane (100 ml) were stirred at 25° C. for 12 hours. After releasing the pressure, the reaction was worked up and the product was isolated and purified as in Example 1. The content of silylcarbonylation product was about 92%. Yield: 75%, with a 24:1 Z:E ratio.

In a similar manner, various other alkynes and silanes were used in the reaction. Results are shown in Table 2, as Examples XII through XVIII.

TABLE 1

SILYCARBONYLACTION UNDER ONE ATMOSPHERE PRESSURE OF CO

| Example No. | Aklyne | Silane | Silycarbonylated Product | Yield % | Z:E isomer ratio | Silylcarbonylation: Hydrosilylation ratio |
|---|---|---|---|---|---|---|
| I | Ph—C≡CH | $Et_3SiH$ | $Et_3SiCH=C(Ph)CHO$ | 82 | 10:1 | >99:1 |
| II | 4-isobut.Ph—C≡CH | $Me_2PhSiH$ | $Me_2PhSiCH=C(4-isobut.Ph)CHO$ | 74 | 11:1 | >99:1 |
| II | P-tol-C≡CH | $Me_2PhSiH$ | $Me_2PhSiCH=C(p-tolyl)CHO$ | 84 | 38:1 | >99:1 |
| IV | 6-MeO Naph-2-C≡CH | $Me_2PhSiH$ | $Me_2PhSiCH=C(2-nAPH-6OMe)CHO$ | 95 | 11:1 | >99:1 |
| V | n-Hex—C≡CH | $Me_2PhSiH$ | $Me_2PhSiCH=C(n-Hex)CHO$ | 81 | 14:1 | >99:1 |
| VI | $AcOCH_2C≡CH$ | $Et_3SiH$ | $Et_3SiCH=C(CH_2OAc)CHO$ | 71 | 29:1 | >96:4 |
| VII | $MeOCH_2C≡CH$ | $Et_3SiH$ | $Et_3SiCH=C(CH_2OMe)CHO$ | 87 | 14:1 | >99:1 |
| VIII | $Me_2C-C≡CH$ <br> \| <br> OH | $Et_3SiH$ | $Et_3SiCH=C(CMe_2)CHO$ <br> \| <br> OH | 41 | 24:1 | 91:9 |
| IX | Ph—C≡C—Ph | $Et_3SiH$ | $Et_3SiC(Ph)=C(Ph)CHO$ | 95 | 32:1 | 71:29 |
| X | Ph—C≡C—$CH_3$ | $Et_3SiH$ | $Et_3SiC(CH_3)=C(Ph)CHO$ | 72 | 40:1 | 56:42 |

TABLE 2

SILYCARBONYLACTION UNDER LO ATMOSPHERE PRESSURE OF CO

| Example No. | Aklyne | Silane | Silycarbonylated Product | Yield % | Z:E isomer ratio | Silylcarbonylation: Hydrosilylation ratio |
|---|---|---|---|---|---|---|
| XI | PhC≡CH | $Et_3SiH$ | $Et_3SiCH=C(Ph)CHO$ | 75 | 24:1 | 92:8 |
| XII | 4-isobut.Ph—C≡CH | $Et_3SiH$ | $Et_3SiCH=(4-isobut.Ph)CHO$ | 72 | 10:1 | 96:4 |
| XIII | P-tolylC≡CH | $Et_3SiH$ | $Et_3SiCH=C(p-tolyl)CHO$ | 63 | 17:1 | 96:4 |
| XIV | n-HexylC≡CH | $Et_3SiH$ | $Et_3SiCH=C(n-hexyl)CHO$ | 81 | 35:1 | >99:1 |
| XV | $AcOCH_2C≡CH$ | $Et_3SiH$ | $Et_3SiCH=C(CH_2OAc)CHO$ | 51 | 22:1 | >99:1 |
| XVI | $MeOCH_2C≡CH$ | $Et_3SiH$ | $Et_3SiCH=C(CH_2OMe)CHO$ | 77 | 30:1 | >99:1 |

TABLE 2-continued

SILYCARBONYLACTION UNDER LO ATMOSPHERE PRESSURE OF CO

| Example No. | Aklyne | Silane | Silycarbonylated Product | Yield % | Z:E isomer ratio | Silylcarbonylation: Hydrosilylation ratio |
|---|---|---|---|---|---|---|
| XVII | Me$_2$C—C≡CH<br>\|<br>OH | Et$_3$SiH | Et$_3$SiCH=C(CMe$_2$)CHO<br>\|<br>OH | 36 | 36:1 | 92:8 |
| XVIII | MeCC≡CH<br>\|\|<br>O | Et$_3$SiH | Et$_3$SiCH≡C(COMe)CHO | 47 | 2:1 | >99:1 |

What is claimed is:

1. A process to regioselectively prepare silylcarbonylated derivatives of a 1-alkyne, comprising:
    (a) combining with a suitable solvent a catalyst, a 1-alkyne, carbon monoxide, and an organosilane of the formula SiHR$_1$R$_2$R$_3$ to form a reaction mixture, wherein said catalyst is a carboxylate salt of rhodium, iridium, or rhenium, and wherein R$_1$, R$_2$, and R$_3$ could be the same or different and are selected from the group consisting of hydrogen, a C$_1$–C$_6$ alkyl, a phenyl group, a naphthyl group and an alkoxy of the formula —OR' wherein R' is a C$_1$–C$_6$ alkyl, provided at least one of said R$_1$, R$_2$ and R$_3$ is not hydrogen; and
    (b) silylcarbonylating said 1-alkyne in said reaction mixture at a temperature and pressure operative to produce predominantly the Z-isomer of said silylcarbonylated derivative with a substantial absence of hydrosilylated by-product.

2. The process as described in claim 1, wherein said Z-isomer forms at least 99% of said silylcarbonylated derivative.

3. The process as described in claim 1, wherein said Z-isomer forms at least 90% of said silylcarbonylated derivative.

4. The process as described in claim 1, wherein said hydrosilylated by-products form in not more than 10% yields in the process.

5. The process as described in claim 1, wherein said 1-alkyne is of the formula, R—C≡CH, wherein R is a branched or unbranched C$_1$–C$_8$ alkyl, or a branched or unbranched C$_1$–C$_8$ alkoxy or a substituted or unsubstituted phenyl or naphthyl moiety, wherein the substituents are selected from the group consisting of alkyl, phenyl, benzyl, benzoyl, alkoxy, acetamido, halo, hydroxy, dialkylamino and acetoxy groups, wherein the alkyl component is a branched or unbranched C$_1$–C$_8$ alkyl moiety.

6. The process as described in claim 5, wherein said R moiety is 4'-isobutylphenyl.

7. The process as described in claim 1, wherein said 1-alkyne is 6-methoxynapthyl-2-acetylene.

8. The process as described in claim 1, wherein said catalyst is selected from the group consisting of rhodium acetate, rhodium butyrate, rhodium (II)trifluoroacetate and dirhodium (II) perfluorobutyrate.

9. The process as described in claim 8, wherein said catalyst is dirhodium (II) perfluorobutyrate.

10. The process as described in claim 1, wherein said solvent is selected from the group consisting of hydrocarbons, ethers, esters, halogenated hydrocarbons, amides and ketones.

11. The process as described in claim 10, wherein said solvent is a halogenated hydrocarbon.

12. The process as described in claim 10, wherein said solvent is dichloromethane.

13. The process as described in claim 1, wherein said organosilane is selected from the group consisting of triethylsilane, trimethylsilane, tributylsilane, triphenylsilane and phenyldimethylsilane.

14. The process as described in claim 13, wherein said organosilane is triethylsilane.

15. The process as described in claim 13, wherein said organosilane is phenyldimethylsilane.

16. The process as described in claim 1, wherein said operative temperature is in the range of about −30° C. to about 200° C. and said operative pressure is one atmosphere of carbon monoxide.

17. The process as described in claim 1, wherein said operative temperature is in the range about −30° C. to about 300° C. and said operative pressure is about 2–20 atmospheres of carbon monoxide.

18. A process to regioselectively prepare silylcarbonylated product of a 1-alkyne comprising the steps in combination:
    (a) preparing a mixture including a carboxylate salt of a metal selected from the group consisting of rhodium, iridium, and rhenium, in a suitable solvent;
    (b) adding to said mixture a silane of the formula SiHR$_1$R$_2$R$_3$ wherein R$_1$, R$_2$, and R$_3$ could be the same or different and are selected from the group consisting of hydrogen, a C$_1$–C$_6$ alkyl, a phenyl group, a naphthyl group and an alkoxy of the formula —OR' wherein R' is a C$_1$–C$_6$ alkyl, provided at least one of said R$_1$, R$_2$ and R$_3$ is not hydrogen;
    (c) providing carbon monoxide to said mixture; and
    (d) adding to said mixture a 1-alkyne, wherein said 1-alkyne is silylcarbonylated to the substantial exclusion of hydrosilylated by-products, and wherein said silylcarbonylated product is predominantly in the Z-form.

19. The process as described in claim 18, wherein said silylcarbonylation is performed at about −30° C. to about 200° C., and at a pressure of about one atmosphere of carbon monoxide.

20. The process as described in claim 18, wherein said silylcarbonylation is performed at about −30° C. to about 300° C., and at a pressure of about 2–20 atmospheres of carbon monoxide.

21. A process to regioselectively prepare silylcarbonylated product of a 1-alkyne, the process sequentially comprising:
    (a) providing a first mixture comprising a catalyst, an organosilane, carbon monoxide and a suitable solvent, wherein said catalyst is a carboxylate salt of a metal selected from the group consisting of rhodium, iridium, and rhenium, and wherein said organosilane is of the formula SiHR$_1$R$_2$R$_3$ wherein $R_1$, $R_2$, and $R_3$ could be the same or different and are selected from the group consisting of hydrogen, a $C_1$–$C_6$ alkyl, a phenyl group, a naphthyl group and an alkoxy of the formula —OR' wherein R' is a $C_1$–$C_6$ alkyl, provided at least one of said $R_1$, $R_2$ and $R_3$ is not hydrogen;

(b) adding a 1-alkyne to the first mixture, and stirring under one atmosphere pressure of carbon monoxide; and (c) separating the silylcarbonylated product formed in the reaction, wherein said 1-alkyne is silylcarbonylated to the substantial exclusion of hydrosilylated by-products, and wherein said silylcarbonylated product is predominantly in the Z-form.

* * * * *